United States Patent
Ghelli et al.

(10) Patent No.: US 6,899,693 B2
(45) Date of Patent: May 31, 2005

(54) PULSATING PUMPING UNIT FOR A FLUID, PARTICULARLY BLOOD

(75) Inventors: Nicola Ghelli, S. Pietro in Casale (IT); Fabrizio Mastrantonio, Rome (IT); Ivo Panzani, Mirandola (IT)

(73) Assignee: Dideco S.p.A., Mirandola (IT)

( * ) Notice: Subject to any disclaimer, the term of this patent is extended or adjusted under 35 U.S.C. 154(b) by 307 days.

(21) Appl. No.: 09/921,012

(22) Filed: Aug. 2, 2001

(65) Prior Publication Data

US 2002/0057990 A1 May 16, 2002

(30) Foreign Application Priority Data

Aug. 8, 2000 (IT) ..................................... MI2000A1853

(51) Int. Cl.[7] .............................................. A61M 37/00
(52) U.S. Cl. ............................ 604/6.11; 604/6.1; 604/9
(58) Field of Search ........................... 417/437; 604/6.1, 604/6.11, 65, 4.01, 5.01; 261/24; 422/44

(56) References Cited

U.S. PATENT DOCUMENTS

| | | | | |
|---|---|---|---|---|
| 3,403,696 A | * | 10/1968 | Pynchon ................ 137/516.13 |
| 4,662,829 A | * | 5/1987 | Nehring ...................... 417/395 |
| 4,673,393 A | * | 6/1987 | Suzuki et al. .......... 604/167.04 |
| 4,697,989 A | * | 10/1987 | Perlov et al. .................. 417/53 |
| 4,906,229 A | * | 3/1990 | Wampler ...................... 600/16 |
| 5,266,012 A | * | 11/1993 | Hashimoto et al. ......... 417/412 |
| 5,413,599 A | * | 5/1995 | Imachi et al. ............... 623/1.24 |

* cited by examiner

Primary Examiner—Angela D. Sykes
Assistant Examiner—Leslie R. Deak
(74) Attorney, Agent, or Firm—Popovich, Wiles & O'Connell, P.A.

(57) ABSTRACT

A pulsating pumping unit for a fluid, particularly blood, includes means suitable to draw the fluid from an intake connector in order to send it to a outlet connector. The means are contained in an enclosure provided with valves connected to the inlet and the outlet. The valve connected to the outlet has at least one duct passing through the wall of the enclosure, is open at the end that leads into the portion of space. The pumping unit has a flow control element comprising a band of elastic material fixed to the outer wall of the enclosure at the edges, so as to have a blind portion which faces the exit port of the duct and a portion provided with holes which faces the outer wall.

18 Claims, 5 Drawing Sheets

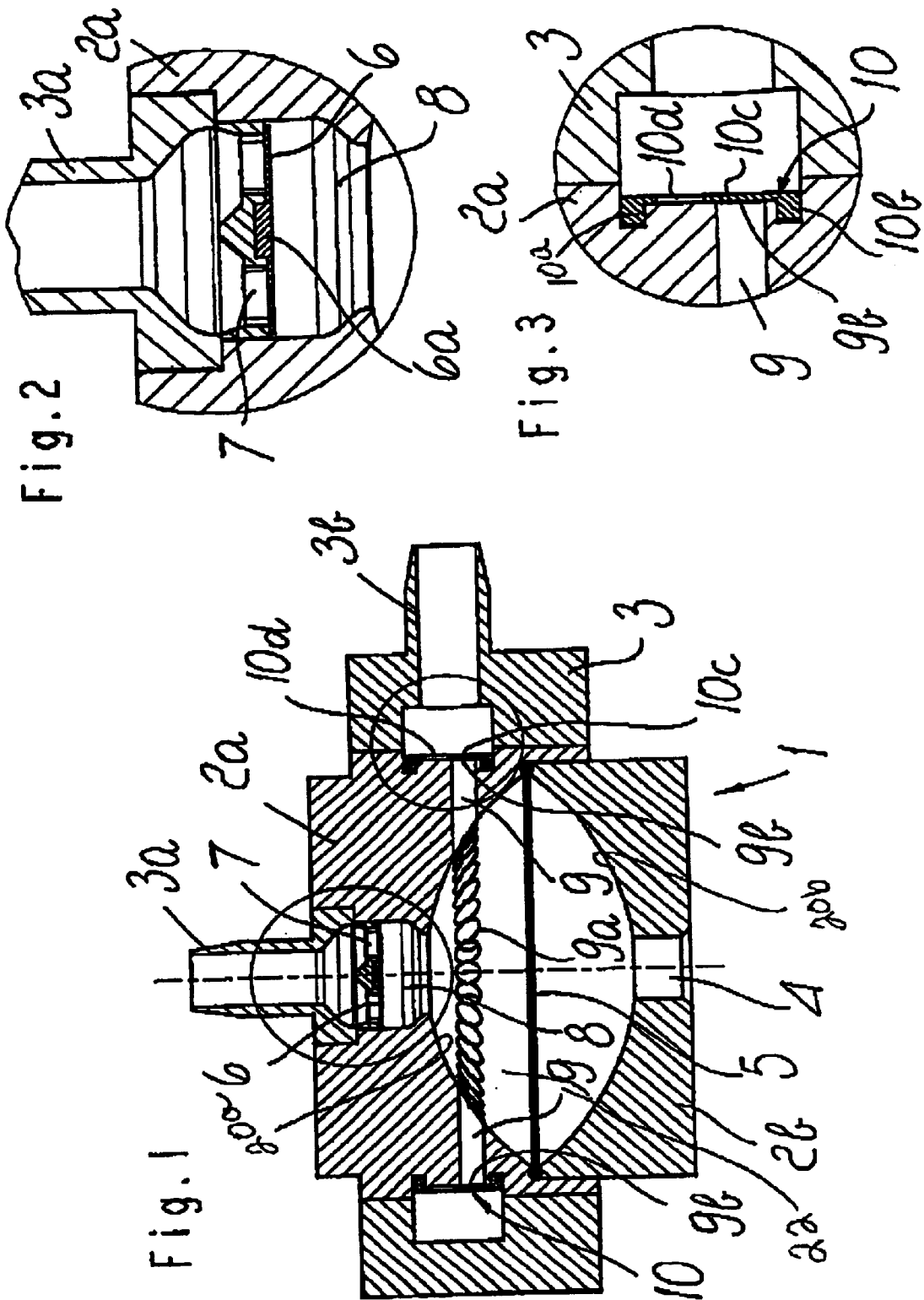

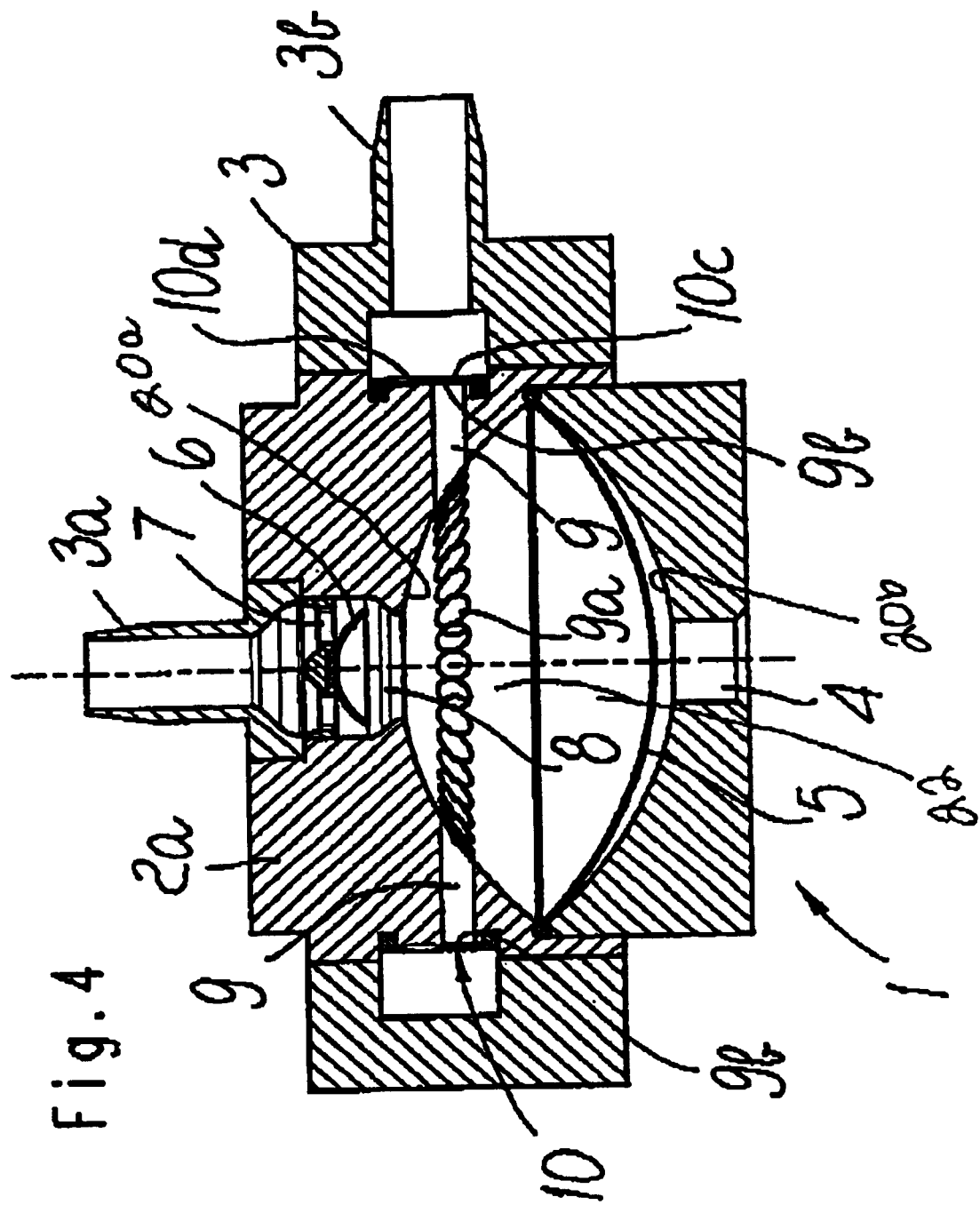

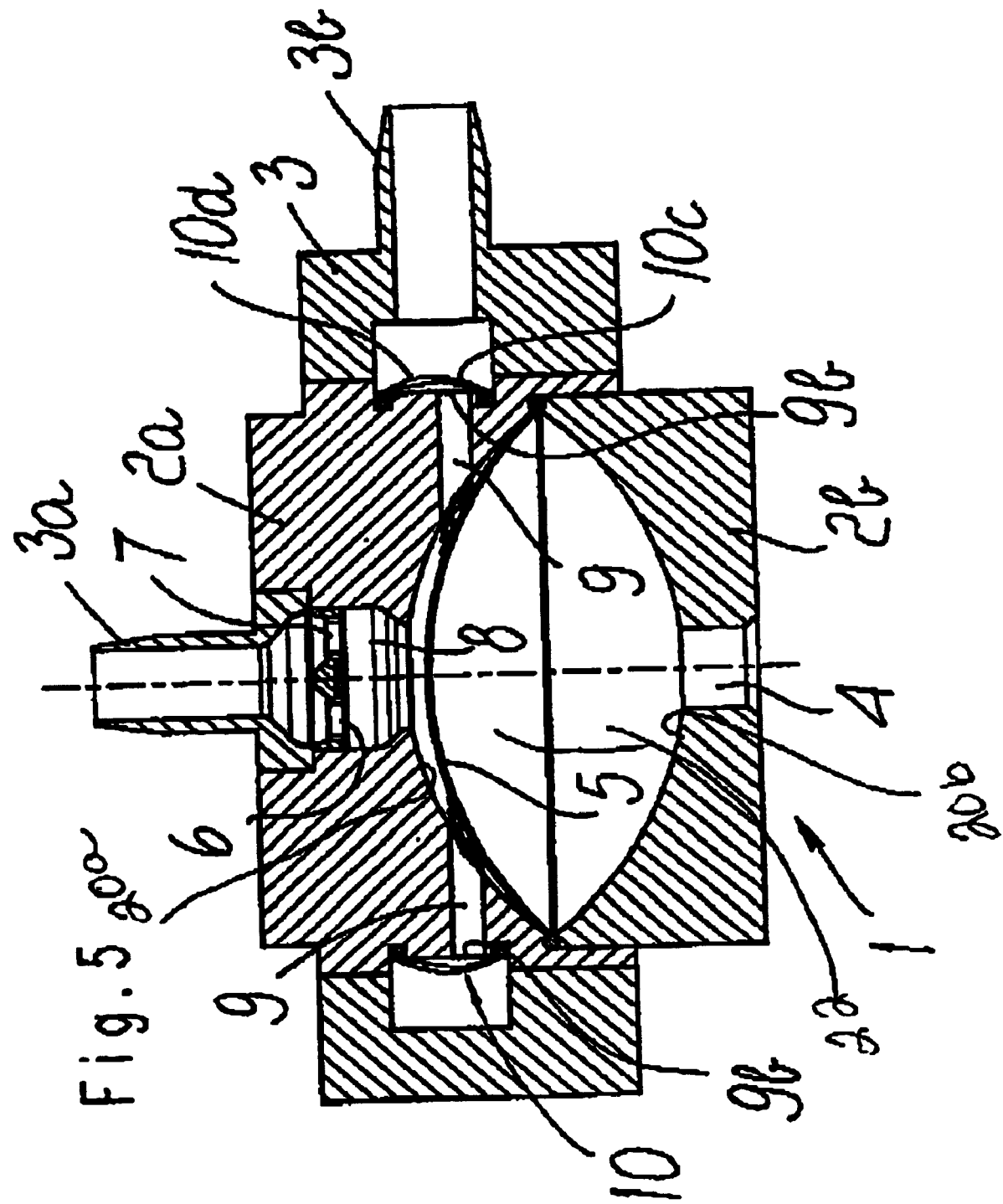

PULSATING PUMPING UNIT FOR A FLUID, PARTICULARLY BLOOD

FIELD OF THE INVENTION

The invention relates to a pulsating pumping unit for a fluid, particularly blood.

BACKGROUND OF THE INVENTION

During many surgical operations it is necessary to provide extracorporeal blood circulation in a circuit which comprises a pump and several other blood treatment devices, such as an oxygenator, a heat exchanger, at least one filter, and a reservoir bag.

The space available in the vicinity of the operating field is notoriously very limited, and therefore the aim of the present invention is to provide a pulsating pumping unit for a fluid, particularly blood, which is highly compact and is suitable to be easily integrated with the other devices of the extracorporeal circuit, so as to be able to achieve maximum reduction of space occupation.

SUMMARY OF THE INVENTION

Within the scope of this aim, an object of the invention is to provide a pumping unit having a simple construction, a modest cost, and maximum reliability in operation.

In a first aspect, this invention is a pump for pumping blood through an extracorporeal circuit, comprising a housing having a wall with an exterior surface and an interior surface, the interior surface defining a pumping chamber; a blood inlet and a blood outlet connected to the pumping chamber, the blood outlet including at least one duct between the interior surface and the exterior surface of the housing; a blood inlet valve; a blood outlet valve comprising flexible material having a peripheral edge affixed to the exterior surface and covering the at least one duct, the flexible material having at least one hole adjacent the exterior surface and spaced from the at least one duct; and means for moving the blood into the pumping chamber through the inlet and out of the pumping chamber through the outlet. Preferably, the pumping chamber is substantially cylindrical. The at least one duct may be a plurality of ducts. These ducts may be arranged radially and may be evenly spaced. The blood inlet valve may comprise a flexible membrane.

In a second aspect, this invention is a pump for pumping blood through an extracorporeal circuit, comprising a housing having a wall with an exterior surface and an interior surface, the interior surface defining a pumping chamber; a flexible membrane having a peripheral edge secured within the pumping chamber, the membrane dividing the pumping chamber into a first side and a second side; a blood inlet and a blood outlet connected to the first side of the pumping chamber, the blood inlet including at least one duct between the interior surface and the exterior surface of the housing; a blood inlet valve; and a blood outlet valve having a flexible section with a peripheral edge affixed to the exterior surface and covering the at least one duct, the flexible section having at least one hole adjacent the exterior surface and spaced from the at least one duct.

In a third aspect, this invention is a pump for pumping blood through an extracorporeal circuit, comprising a housing including a first portion and a second portion, the first portion having a wall with a first interior surface and a first exterior surface, the second portion having a wall with a second interior surface and a second exterior surface, the first and second portions being positioned such that the first and second interior surfaces define a pumping chamber; a flexible membrane positioned in the pumping chamber, the membrane having a peripheral edge which is affixed between the first and second portions of the housing, the membrane dividing the pumping chamber into a first side adjacent the first interior surface and a second side adjacent the second interior surface; a blood inlet connected to the first side of the pumping chamber; a blood inlet valve for controlling the flow of blood through the blood inlet; and a blood outlet connected to the first side of the pumping chamber, the blood outlet including at least one duct through the wall of the first portion; a blood outlet valve including a flexible portion having a peripheral edge affixed to the first exterior surface, the flexible portion having at least one hole adjacent the first exterior surface and spaced from the at least one duct, the outlet valve being configured such that the at least one duct is closed by the outlet valve in the presence of negative pressure in the pumping chamber and is open in the presence of positive pressure in the pumping chamber.

In a fourth aspect, this invention is an integrated blood pump and oxygenator for use in an extracorporeal blood circuit comprising an oxygenator having a substantially cylindrical housing defining an oxygenation chamber containing a plurality of hollow fibers, the oxygenation chamber having a gas inlet and outlet communicating with the lumens of the hollow fibers and a blood inlet and outlet communicating with an exterior of the hollow fibers, the blood inlet including a substantially continuous circumferential opening in the oxygenation chamber; a blood pump having a housing having a wall with an exterior surface and an interior surface, the interior surface defining a pumping chamber; a flexible membrane having a peripheral edge secured within the pumping chamber, the membrane dividing the pumping chamber into a first side and a second side; a blood inlet and a blood outlet, the blood outlet including a plurality of ducts between the interior surface and the exterior surface of the housing; a blood inlet valve; and a blood outlet valve having a flexible section with a peripheral edge affixed to the exterior surface and covering the plurality of ducts, the flexible section having at least one hole adjacent the exterior surface and spaced from the plurality of ducts, the blood outlet of the pump being connected to the blood inlet of the oxygenator, the ducts being spaced radially such that during use blood is uniformly distributed among the hollow fibers.

BRIEF DESCRIPTION OF THE DRAWINGS

Further characteristics and advantages will become apparent from the description of a preferred but not exclusive embodiment of the invention, illustrated only by way of non-limiting example in the accompanying drawings, wherein:

FIG. 1 is a sectional view of the pumping unit in its inactive state.

FIGS. 2 and 3 are detailed views of portions of the pumping unit shown in FIG. 1.

FIGS. 4 and 5 are sectional views of the pumping unit of the invention, illustrating intake and delivery of blood, respectively.

BRIEF DESCRIPTION OF THE PREFERRED EMBODIMENTS

Figure 6:
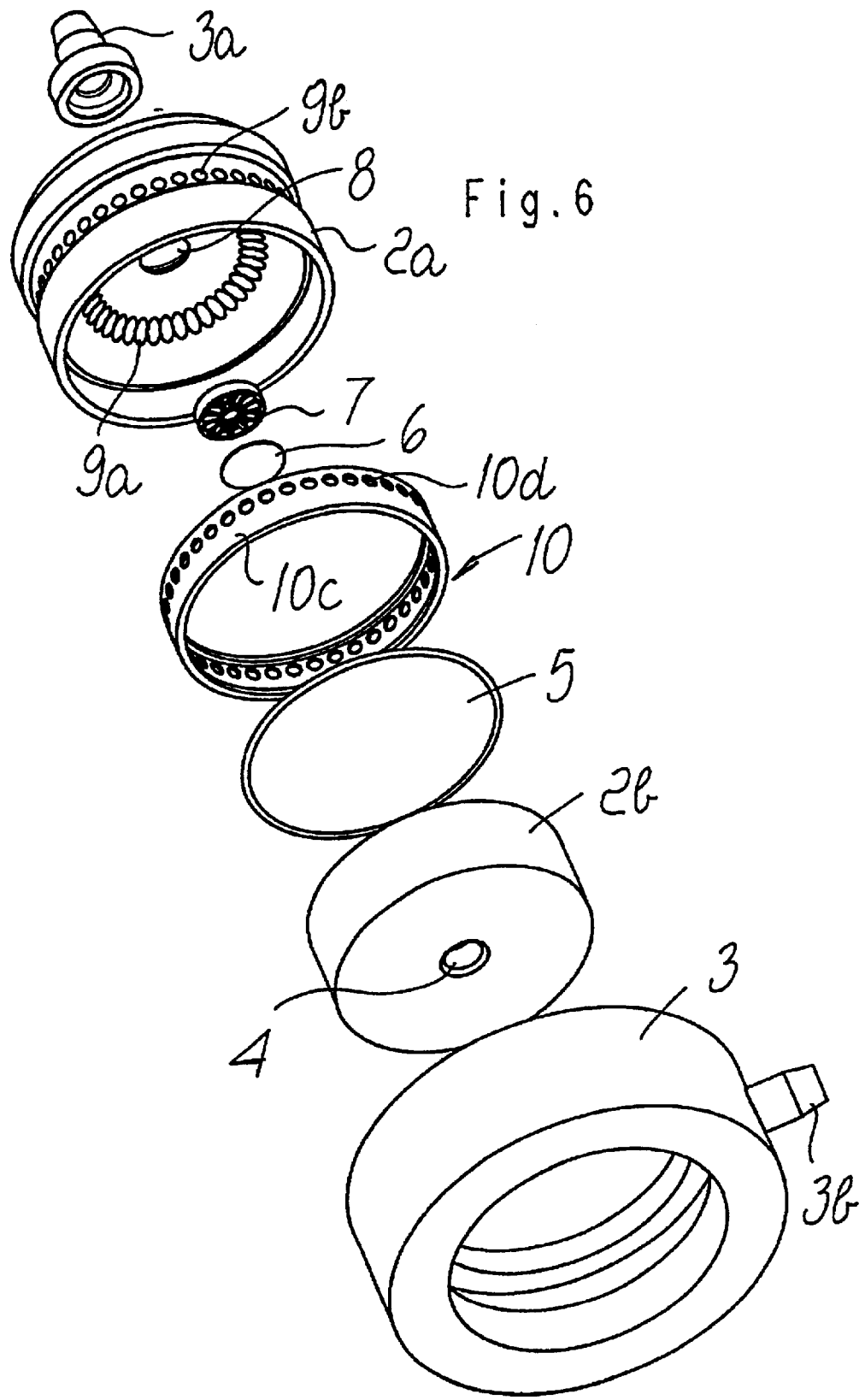
FIG. 6 is an exploded view of the pumping unit of the invention.

With reference to the FIGS. 1 to 7, numeral 1 generally designates the pumping unit. An enclosure or housing 2 is formed by upper portion 2a, which comprises a pump inlet or intake connector 3a, and by lower portion 2b. Housing 2 is provided with outer ring 3, which comprises a pump outlet or delivery connector 3b. Outer ring 3 is rigidly coupled to the enclosure, by, for example, force-fit keying or by means of a film of adhesive.

Within enclosure or housing 2 there is a space delimited by two mutually facing interior surfaces 20a and 20b having substantially dome shapes. Interior surfaces 20a and 20b thus form pumping chamber 22. The upper dome (i.e., upper interior surface 20a) is provided with valves which are connected respectively to blood inlet and outlet connectors, described in detail hereinafter, and the lower dome (i.e., lower interior surface 20b) is connected, by means of duct 4, to a line of working fluid, such as air, which is alternately subjected to pressure and suction. The rate of the pressure-suction cycles substantially coincides with the heart rate so that the pump is able to simulate the natural physiologic pumping of the heart.

The pumping chamber contains a means suitable to draw blood from the pump inlet in order to send it to the pump outlet. This means includes elastic membrane 5, which is fixed at its perimeter to the enclosure at the separation plane of the two domes and is clamped in the connection between upper portion 2a and lower portion 2b of the enclosure.

The valve connected to blood intake or inlet connector 3a comprises membrane 6, which is made of elastic material and is associated by press-fit coupling at the central body 6a on support 7, so as to be rigidly coupled thereto. Support 7 also is rigidly coupled to the wall of duct 8 that extends from the dome comprised within upper portion 2a of the enclosure in order to give access to connector 3a.

The valve connected to the blood delivery connector comprises a plurality of radial and coplanar ducts 9 which pass through the wall of upper portion 2a of the enclosure, are uniformly distributed along the entire extension thereof and are open at end 9a which leads into the portion of space delimited by the enclosure.

A flow control element is provided at ports 9b of the ducts that lead onto the outer wall of the enclosure and comprises an annular band of elastic material 10, which is fixed at edges 10a, 10b to the outer wall, so as to have blind portion 10c which faces ports 9b and a portion provided with holes 10d which faces the outer wall. Suitable sealing gaskets are of course provided where necessary. An exploded view of the various elements of the pumping unit is shown in FIG. 6, which also illustrates the substantially cylindrical form of the pumping unit.

The operation of the invention is evident.

From the inactive position shown in FIG. 1, negative pressure of the working fluid below membrane 5 causes the aspiration of the membrane, as shown in FIG. 4. This opens the valve that is connected to intake connector 3a, whose membrane 6 lowers as shown in FIG. 4, and causes the blood to fill the portion of space delimited by the enclosure. During this intake step, ducts 9 of the valve connected to delivery or outlet connector 3b remain closed by portion 10c of annular band 10 that collapses against the outer wall of the enclosure.

The intake step is followed by the delivery step. The working fluid is pressurized, thus moving membrane 5 to the position shown in FIG. 5. This causes the valve connected to intake connector 3a to close and results in the blood in the pumping chamber being expelled through ducts 9, which have opened because annular band 10 has expanded, as shown in FIG. 5, allowing the blood to pass through holes 10d.

Figure 7:
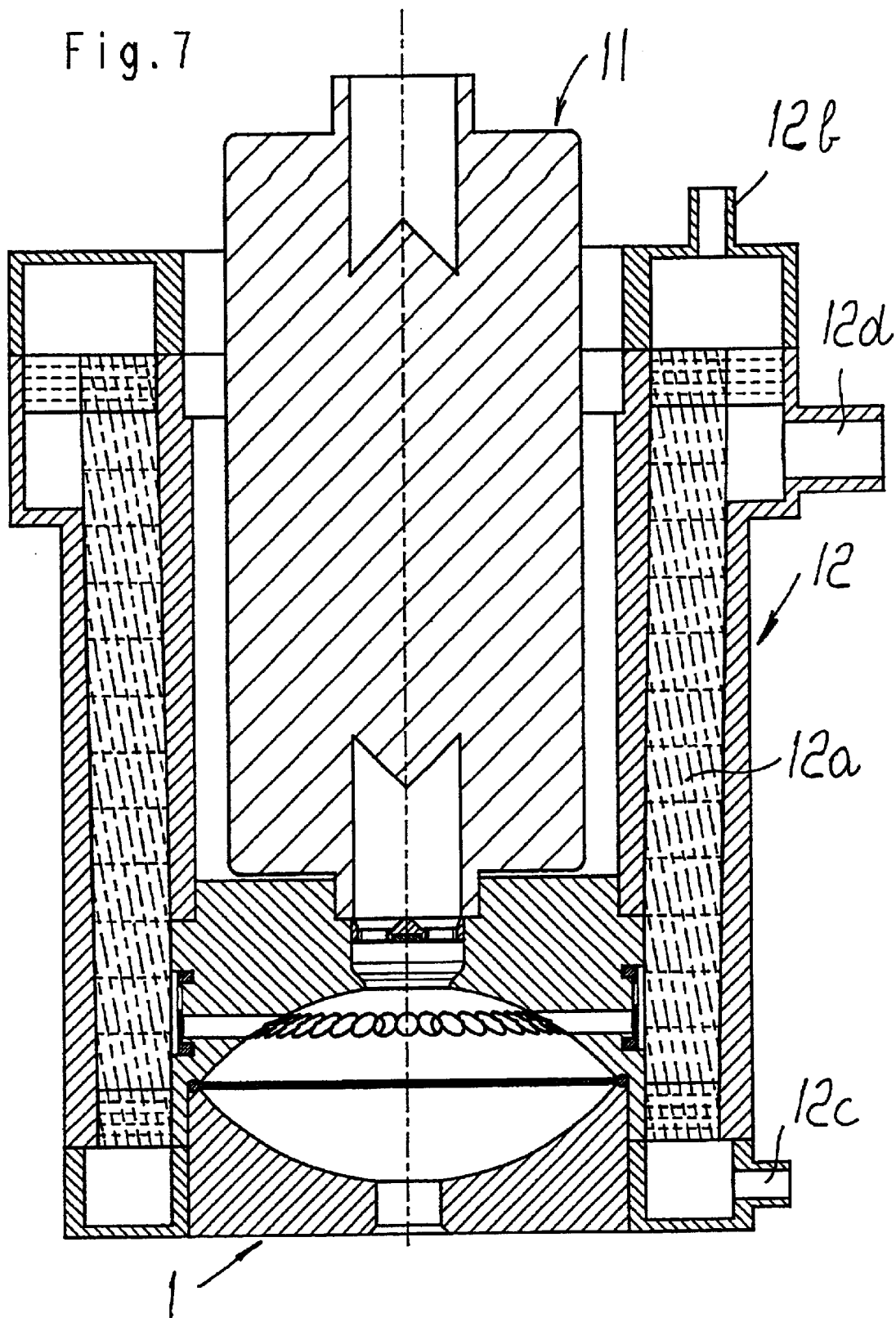
FIG. 7 is a sectional view of the pumping unit integrated into an assembly with an oxygenator and a heat exchanger.

FIG. 7 illustrates the possibility of a high degree of integration with other devices of an extracorporeal blood circuit allowed by the pumping unit according to the invention. This figure shows a cylindrical assembly that includes an oxygenator, pumping unit, and heat exchanger within a single housing. The inlet of pumping unit 1 is directly connected at the outlet of heat exchanger 11. The outlet of pumping unit 1 is connected to the inlet of oxygenator 12. The blood from the oxygenator enters directly from the pumping unit in order to flow over hollow fibers contained in an oxygenation chamber 12a, through which oxygen flows from gas inlet 12b to gas outlet 12c. The blood then exits the oxygenator through outlet 12d. The oxygenation chamber is substantially cylindrical. The pumping unit and heat exchanger are positioned within and are generally surrounded by the oxygenator.

FIG. 7 illustrates that the assembly is highly compact, with maximum reduction of space occupation, and also shows the synergy that occurs in the coupling of the pumping unit in the described embodiment, which has ducts 9 uniformly distributed along the entire wall of the enclosure, with oxygenator 12, which is filled by the blood with uniform distribution along the hollow fibers.

Attention is also called, however, to the compactness that characterizes pumping unit 1 per se, especially by virtue of the configuration of the space that is delimited by the two facing spherical domes (i.e., interior surfaces 20a and 20b), which is divided by elastic membrane 5 arranged at the separation plane of the domes.

The described invention is susceptible of numerous modifications and variations, all of which are within the scope of the inventive concept. Thus, for example, the means suitable to draw the fluid from the inlet and send it to the outlet may vary and the ducts comprised within the valve connected to the delivery of the fluid can assume any shape and direction. The ducts may furthermore be distributed only at part of the wall of the enclosure.

What is claimed is:

1. A pump for pumping blood thorough an extracorporeal circuit, comprising:
    a housing having a wall with an exterior surface and an interior surface, the interior surface defining a pumping chamber;
    a blood inlet and a blood outlet connected to the pumping chamber, the blood outlet including at least one duct between the interior surface and the exterior surface of the housing;
    a blood inlet valve;
    a blood outlet valve comprising flexible material having a peripheral edge affixed to the exterior surface and covering the at least one duct, the flexible material having at least one hole adjacent the exterior surface and spaced from the at least one duct; and
    means for moving the blood into the pumping chamber through the inlet and out of the pumping chamber through the outlet.

2. The pump of claim 1 wherein the pumping chamber is substantially cylindrical.

3. The pump of claim 1 wherein the at least one duct is a plurality of ducts.

4. The pump of claim 3 wherein the ducts are arranged radially.

5. The pump of claim 3 wherein each duct of the plurality of ducts is evenly spaced.

6. The pump of claim 1 wherein the blood inlet valve comprises a flexible membrane.

7. A pump for pumping blood through an extracorporeal circuit, comprising:
- a housing having a wall with an exterior surface and an interior surface, the interior surface defining a pumping chamber;
- a flexible membrane having a peripheral edge secured within the pumping chamber the membrane dividing the pumping chamber into a first and a second side;
- a blood inlet and a blood outlet connected to the first side of the pumping chamber, the blood inlet including at least one duct between the interior surface and the exterior surface of the housing;
- a blood inlet valve; and
- a blood outlet valve having a flexible section with a peripheral edge affixed to the exterior surface and covering the at least one duct, the flexible section having at least one hole adjacent the exterior surface and spaced from the at least one duct.

8. The pump of claim 7 wherein the pumping chamber is substantially cylindrical.

9. The pump of claim 7 wherein the at least one duct is a plurality of ducts.

10. The pump of claim 9 wherein the ducts are arranged radially.

11. The pump of claim 7 wherein each duct of the plurality of ducts is evenly spaced.

12. The pump of claim 7 wherein the blood inlet valve comprises a flexible membrane.

13. A pump for pumping blood through an extracorporeal circuit, comprising:
- a housing including a first portion and a second portion, the first portion having a wall with a first interior surface and a first exterior surface, the second portion having a wall with a second interior surface and a second exterior surface, the first and second portions being positioned such that the first and second interior surfaces define a pumping chamber;
- a flexible membrane positioned in the pumping chamber, the membrane having a peripheral edge which is affixed between the first and second portions of the housing, the membrane dividing the pumping chamber into a first side adjacent the first interior surface and a second side adjacent the second interior surface;
- a blood inlet connected to the first side of the pumping chamber;
- a blood inlet valve for controlling the flow of blood through the blood inlet;
- a blood outlet connected to the first side of the pumping chamber, the blood outlet including at least one duct through the wall of the first portion; and
- a blood outlet valve including a flexible portion having a peripheral edge affixed to the first exterior surface, the flexible portion having at least one hole adjacent the first exterior surface and spaced from the at least one duct, the outlet valve being configured such that the at least one duct is closed by the outlet valve in the presence of negative pressure in the pumping chamber and is open in the presence of positive pressure in the pumping chamber.

14. The pump of claim 13 wherein the pumping chamber is substantially cylindrical.

15. The pump of claim 13 wherein the at least one duct is a plurality of ducts.

16. The pump of claim 15 wherein the ducts are arranged radially.

17. The pump of claim 15 wherein each duct of the plurality of ducts is evenly spaced.

18. The pump of claim 13 wherein the blood inlet valve comprises a flexible membrane.

* * * * *